United States Patent
Wang

(10) Patent No.: US 6,238,696 B1
(45) Date of Patent: May 29, 2001

(54) PROCESS FOR PROVIDING HERBAL MEDICANTS IN CELLULOSE DERIVATIVE CAPSULES

(75) Inventor: Xiping Wang, Brevard, NC (US)

(73) Assignee: GAIA Herbs, Inc., Brevard, NC (US)

( * ) Notice: Subject to any disclaimer, the term of this patent is extended or adjusted under 35 U.S.C. 154(b) by 0 days.

(21) Appl. No.: 09/478,880

(22) Filed: Jan. 7, 2000

(51) Int. Cl.⁷ .............................. A61K 9/48; A01N 65/00
(52) U.S. Cl. .................. 424/452; 424/195.1; 424/425; 424/456
(58) Field of Search .................... 424/452, 455, 424/456, 195.1

(56) References Cited

U.S. PATENT DOCUMENTS

| | | |
|---|---|---|
| 4,918,099 | 4/1990 | Moon . |
| 4,931,362 * | 6/1990 | Zsifkovits et al. ............ 424/462 |
| 5,063,057 * | 11/1991 | Spellman et al. ............ 424/456 |
| 5,082,661 * | 1/1992 | Melnik et al. ............... 424/456 |
| 5,318,798 * | 6/1994 | Uchida et al. ............... 424/452 |
| 5,330,835 * | 7/1994 | Kikuchi et al. ............. 424/452 |
| 5,384,121 | 1/1995 | Rhodes . |
| 5,417,979 | 5/1995 | Fan et al. . |
| 5,560,913 * | 10/1996 | Kupper .................... 424/195.1 |
| 5,569,466 * | 10/1996 | Tanner et al. ............... 424/452 |
| 5,578,307 * | 11/1996 | Wunderlich et al. .......... 424/195.1 |
| 5,614,197 | 3/1997 | Pathak et al. . |
| 5,622,704 | 4/1997 | Hacker et al. . |
| 5,624,673 | 4/1997 | Bonte et al. . |
| 5,631,001 | 5/1997 | Harich et al. . |
| 5,646,178 | 7/1997 | Walker et al. . |
| 5,741,491 | 4/1998 | Jones . |
| 5,747,050 | 5/1998 | Tolpa et al. . |
| 5,869,060 | 2/1999 | Yoon et al. . |
| 5,891,464 | 4/1999 | Bonte et al. . |

* cited by examiner

*Primary Examiner*—Herbert J. Lilling
(74) *Attorney, Agent, or Firm*—Myers, Bigel, Sibley & Sajovec, P.A.

(57) ABSTRACT

The present invention relates to a process for providing non-lipid, liquid form herbal extracts in a vegetable gelatin, HPMC, or any other cellulose derivative capsule. The process includes extracting an herbal plant material with an alcohol to provide an aqueous alcoholic herbal extract. The aqueous alcoholic herbal extract is contacted with sufficient glycerin to maintain the extract preferably in solution, and at least dispersed in the mixture of glycerin and aqueous alcoholic herbal extract. Alcohol and water is removed form the mixture to provide a glycerin-based liquid or semi-solid herbal extract and having a moisture content of less than 10 percent by weight, and preferably less than 5 percent by weight. The herb extract is then encapsulated in a vegetable gelatin, HPMC, or any other cellulose derivative capsule.

14 Claims, No Drawings

PROCESS FOR PROVIDING HERBAL MEDICANTS IN CELLULOSE DERIVATIVE CAPSULES

FIELD AND BACKGROUND OF THE INVENTION

The present invention relates to a process of providing herbal extracts in cellulose derivative capsules, and more particularly, liquid herbal medicants in vegetable gelatin, hydroxypropyl methylcellulose ("HPMC"), or any other cellulose derivative capsules.

Herbal remedies, also sometimes referred to as phytopharmaceuticals or dietary supplements, are becoming more and more popular as alternatives to conventional pharmaceuticals. Such herbal remedies are regarded as being more naturally healthier than conventional pharmaceuticals. Throughout the world every culture has a long history of using herbs in everyday medical treatment. For example, it is known that antidepressive activity is attributed to St. John's wort. U.S. Pat. No. 5,622,704 to Hacker proposes using a combination of Rhizoma zingiberis and Ginkgo biloba to treat anxiety. Healthy immune function is often attributed to the use of Echinacea. Thousands of well researched scientific and university studies document the efficacy of herbal remedies.

The delivery system through which an herb is ingested plays a significant role in the way and the extent to which the herb is metabolized. Previously herbs were administered as crude plant material in either capsule or tablet form. More recently powdered 'standardized' extracts have been recognized as botanicals that deliver more and specified potency. Herbal extracts in a fixed oil base filled into gelatin capsule have received little recognition. Problems of miscibility and absorption are numerous with such systems.

It has been suggested by many pharmaceutical companies that a liquid delivery system is a superior method of administering therapeutic remedies. Yet non-lipid base liquid botanical standardized extracts in capsule form have not been available due to the problem maintaining the capsule integrity once the liquid is filled into the capsule.

SUMMARY OF THE INVENTION

Consumer demand for capsules made from vegetable sources is increasing rapidly today. This invention specifies the procedures of providing a non-lipid, liquid herbal extract in a sealed cellulose derivative capsule such as vegetable gelatin or HPMC. This technology demonstrates the unique methods and processes utilized in extraction that enable the liquid herbal extract and vegetable gelatin, HPMC, or any other cellulose derivative capsule to remain stable without degradation once the liquid is filled into the capsule.

Specifically, the present invention relates to a process for providing non-lipid, liquid-form herbal extracts in a vegetable gelatin, HPMC, or any other cellulose derivative capsule. The process includes extracting an herbal plant material with an alcohol or aqueous/alcohol to provide an aqueous alcoholic herbal extract. This aqueous alcoholic herbal extract is transferred to a liquid glycerin-based herbal extract through rotary evaporation or other condensing equipment. This transfer of solution is accomplished by adding vegetable glycerin while the water and alcohol are being evaporated. The herbal extract is maintained in solution or dispersed in the alcohol mixture. The resulting herbal extract contains a moisture content of no more than 10 percent by weight, and preferably no more than 5 percent by weight. The herb extract is then encapsulated in vegetable gelatin, HPMC, or any other cellulose derivative capsule. A selected bio-active marker compound is measured after the step of extraction and after the step of removing water and alcohol.

DETAILED DESCRIPTION OF THE INVENTION

As discussed above, an herbal plant material is provided. The herbal material is preferably in the form of whole leaf, stem, stalk, root and the like, and is ground or cut prior to treatment. The herbal materials can be organic, cultivated, or wild. Suitable herbal materials include, but are not limited to, kava kava, echinacea, St. John's wort, valerian root, milk thistle seed, Siberian ginseng, nettle leaf, ginkgo, gotu kola, ginkgo/gotu kola supreme, astragalus, goldenseal, dong quai, ginseng, St. John's wort supreme, echinacea/goldenseal supreme, bilberry, green tea, hawthorne, ginger, turmeric, black cohosh, cats claw, chamomile, dandelion, chaste tree berry, feverfew, garlic, horse chestnut, licorice, eyebright, yohimbe, astragalus supreme, valerian poppy supreme, and serenity elixir. The herbal material is then extracted with an aqueous alcohol in different concentrations to provide an aqueous alcoholic herbal extract. Suitable alcohols include $C_1$ to $C_3$ alcohols like ethanol. Preferably, ethanol is used. The alcohol can be a co-solvent mixture such as a mixture of alcohol and water. During extraction, the herbal material is preferably percolated or macerated to facilitate extraction.

The aqueous alcoholic herbal extract is monitored for its bio-activity. As used herein, bio-activity is defined as qualitative and quantitative measurement of the marker compounds. The methodology for measuring the bio-activity may change from herb to herb. A trained Natural Products Chemist develops the methodology or uses accepted reference methodologies.

After extraction, sufficient glycerin is added to adjust the bio-activity required to complete the standardization of the formulation. Typically from 20 to 80 percent by weight of glycerin is contained in the finished product. The mixture of aqueous alcoholic herb extract and glycerin mixture is condensed or concentrated, using any one of the various condensation techniques known to those skilled in the art. For example, rotary evaporation under reduced pressure in a warm water bath at a temperature of from about 55° to 85° C. can be used.

The herb extract having a moisture content of less than 10 percent is then encapsulated in a cellulose derivative capsule. Suitable cellulose include, but are not limited to, vegetable gelatin and hydroxylalkyl celluloses including methylcellulose, carboxymethylcellulose, hydroxypropylcellulose, and the preferred hydroxypropyl methylcellulose ("HPMC"). Suitable capsules are available from many sources, and sizes from "00" to "3" are preferably used. Suitable excipients may be added to the extract prior to encapsulation and may include vegetable oils, waxes, lecithin, fats, semi-solid and liquid polyols and the like. Preferably, no excipients other than lecithin are needed. Suitable encapsulation equipment is available from market suppliers such as Shionogi. Air can be eliminated from the capsules using an inert gas such as nitrogen.

EXAMPLES

The following specific examples are provided to afford a better understanding of the present invention to those skilled in the art. It is to be understood that these samples are intended to be illustrative only and are not intended to limit the invention in any way.

Example 1

Preparation of Echinacea Supreme:

The aqueous alcohol extracts of *Echinacea angustifolia* root, *Echinacea purpurea* root, *Echinacea purpurea* flower, and *Echinacea purpurea* seed are prepared by extracting each individul herbal material separately with aqueous ethyl alcohol in different concentration. The following materials are used:

|  | L |
| --- | --- |
| *Echinacea angustifolia* root aqueous alcoholic extract | 120 |
| *Echinacea purpurea* root aqueous alcoholic extract | 151 |
| *Echinacea purpurea* flower aqueous alcoholic extract | 125 |
| *Echinacea purpurea* seed aqueous alcoholic extract | 64 |

The aqueous alcoholic extracts are filtered through a fine screen (100 mesh). The concentration of isobutylamides of each of the extracts is measured and should be at least 0.3 mg/ml. A 100 L round bottom flask is loaded with 7 L of glycerin. To this, 460 L of Echinacea aqueous alcoholic extract is gradually injected and condensed until the extract has a moisture content of 5 percent or less.

The concentrated extract is removed from the flask. The glycerin is added to the concentrated extract to bring up the volume of the extract to 55 L. As a monitor of bio-activity, the concentration of total isobutylamides is 2.2 mg/ml or higher. The final product volume is adjusted with glycerin according to the analytical test results to a finished volume of 61 L.

The extract is encapsulated in a size "1" vegetable gelatin capsule and sealed with the same gelatin. Each capsule has 0.41 ml of the Echinacea Supreme extract and the density is from about 0.53 mg/ml to 0.61 mg/ml.

Ten capsules are placed in a jar in 100 percent moisture and 40° C. condition for 90 days. The capsules maintained their stability.

Example 2

Echinacea Goldenseal Supreme:

The following materials are used:

|  | L |
| --- | --- |
| Echinacea supreme | 12 |
| Goldenseal aqueous alcoholic extract | 4 |
| Barberry aqueous alcoholic extract | 9.5 |
| Oregon grape root aqueous alcoholic extract | 9.5 |
| St. John's Wort aqueous alcoholic extract | 7.3 |

Echinacea supreme is obtained from the combination of different Echinacea aqueous alcoholic extracts in different ratios (See Example 1).

The concentration of isobutylamides of the Echinacea supreme is measured and should be at least 1.75 mg/ml. The concentration of alkaloids in the Goldenseal, Barberry and Oregon grape root extracts are measured. The average concentration of the total alkaloids should be at least 3.3 mg/ml. A 100 L rotary evaporator flask is loaded with 7 L of glycerin. The materials listed above is added gradually and concentrated by rotary evaporation until the extract has a moisture content of 5 percent or less.

The concentrated extract is removed from the flask and placed in a container. 11 L glycerin is added to the concentrated extract. As a monitor of bio-activity, the concentration of total isobutylamides is 1 mg/ml or higher and the total alkaloids is 5.5 mg/ml or higher. The additional amount of glycerin is added to the extract if it is needed, according to the analytical test results. The final finished product has a volume of 21 L.

The extract is encapsulated in a size "1" vegetable capsule and sealed with the same gelatin. Each capsule has 0.41 ml of the Standardized Echinacea Goldenseal extract and the density is from about 0.5 mg/ml to 0.6 mg/ml.

Ten capsules are placed in a jar in 100 percent moisture and 40° C. condition for 90 days. The capsules maintained their stability.

Example 3

Preparation of Ginkgo Gotu Kola supreme:

Each individual herbal extract in this example is obtained from the extraction of each herb with different concentrations of ethyl alcohol and spring water. The following materials are used:

|  | L |
| --- | --- |
| Gotu Kola leaf and root aqueous alcoholic extract | 53 |
| Ginkgo leaf aqueous alcoholic extract | 26 |
| Siberian ginseng solid extract | 11 |
| Wild oat milk seed aqueous alcoholic extract | 21 |
| Fo-Ti aqueous alcoholic extract | 15 |
| Peppermint leaf aqueous alcoholic extract | 19 |
| Rosemary leaf aqueous alcoholic extract | 13 |

The aqueous alcoholic herbal extracts are filtered through a fine screen (100 mesh).

A 100 L round bottom flask is loaded with 10 L of glycerin. To this, 158 L of the above aqueous alcoholic herbal extracts are gradually injected and condensed until the mixed extract has a moisture content of 5 percent or less.

The concentration of triterpenoids in Gotu Kola aqueous alcoholic extract is 2 mg/ml, the concentration of ginkgo flavonoid glycosides in Ginkgo leaf aqueous alcoholic extract is 1.8 mg/ml; the concentration of eleutheroside B and eleutheroside E in Siberian Ginseng solid extract is 3.8 mg/ml.

The concentrated extract is removed from the flask. To this concentrated extract mixture is added 30 L of glycerin to a volume of 50 L. As a monitor of bio-activity, the concentration of total flavone glycosides is 1.2 mg/ml and the triterpenoids is 0.44 mg/ml. The glycerin is adjusted according to these results to a finished volume of 57 L.

An amount of 38 L for DS (Standard Double Strength) is removed from the extract, and the remaining 19 L are diluted with 19 L glycerin for S (Standard).

The extract is encapsulated in a size "1" vegetable capsule and sealed with the same gelatin. Each capsule holds 0.41 ml of Ginkgo Gotu Kola Supreme concentrated extract and the density is from about 0.5 mg/ml to 0.6 mg/ml, with an average difference of 1 percent or less.

Ten capsules are placed in a jar in 100 percent moisture and 40° C. conditions for 90 days. The capsules maintained their stability.

Example 4

Preparation of Kava Kava extract for encapsulation:

Kava kava aqueous alcoholic liquid extract is obtained from percolation and/or maceration of the herb with the mixture of grain alcohol and spring water. The following materials are used:

Kava kava aqueous alcoholic extract (30 mg/ml) 302 L

Kava Kava aqueous alcoholic liquid extract is analyzed before concentration for calculation of the volume of the final product, and filtered through a fine screen (100 mesh). A 100 L round bottom flask is loaded with 10 L of glycerin. To this, 302 L of Kava Kava aqueous alcoholic liquid extract is gradually injected and condensed until the extract has a moisture content of 5 percent or less.

The concentrated extract is removed from the flask. To this concentrated extract, 18 L of lecithin and 12 L of glycerin are added, and mix them well. The volume will be 45 L.

A sample is tested for the concentration of kavalactones. A mixture of 55 percent glycerin and 45 percent lecithin is then added according to the test result to a finished volume of 184 mg/ml. The finished product will be 49 L.

The extract is encapsulated in a size "1" vegetable capsule and sealed with the same gelatin. Each capsule holds 0.41 ml of the concentrated Kava Kava extract and the density is from about 0.5 g/ml to 0.6 g/ml, with an average difference of 1 percent or less.

Ten capsules are placed in a jar in 100 percent moisture and 40° C. conditions for 90 days. The capsules maintained their stability.

Example 5

Preparation of Kava Kava extract for encapsulation:

Kava Kava semi-solid extract which is standardized to 55% kavalectones and prepared by the extraction of Kava Kava root and rhizome with aqueous alcohol in different concentration. The following materials are used:

Kava Kava paste 450 g/kg

The Kava Kava semi-solid extract is measured and should weight at least 23.6 kg (equal to 21 L) and placed in a 20 gallon container. To this is added 13.5 L of lecithin and 16.5 L glycerin. The extract is stirred and heated in water bath at a temperature of 80–90° C. until the extract become homogeneous.

A sample of the extract is sent for testing. The concentration of the extract should be at least 170 mg/g or 190 mg/ml. The volume is adjusted with a mixture of lecithin and glycerin in accordance with the test result.

The extract is encapsulated in a size "1" vegetable capsule and sealed with the same gelatin. Each capsule holds 0.41 ml of Kava Kava extract and the density of the extract is from about 500 mg/ml to 600 mg/ml, with an average difference of 1 percent or less.

Ten capsules are placed in a jar in 100 percent moisture and 40° C. conditions for 90 days. The capsules maintained their stability.

Example 6

Preparation of Milk Thistle seed liquid capsule:

Milk Thistle Seed aqueous alcoholic liquid extract obtained from percolation and/or maceration of the herb with grain alcohol and spring water in different concentration. The following materials are used:

| | L |
|---|---|
| Milk Thistle Seed aqueous alcoholic extract | 242 |

The concentration of the bio-active component, silymarins, is measured and is 18 mg/ml.

A 100 L round bottom flask is loaded with 10 L glycerin, to this, 242 L of Milk Thistle seed aqueous alcoholic liquid extract is gradually injected and condensed until it has a moisture content of 5 percent or less.

The concentrated extract is removed from the flask and poured into a container. The extract is combined and mixed with an additional 10 L glycerin. A sample is sent for testing. The concentration of silymarins in this extract should be at least 188 mg/ml. The volume is adjusted in accordance with the test results. The ideal final volume is 23 L.

The extract is encapsulated in a size "0" vegetable capsule and sealed with the same gelatin. Each capsule holds 0.64 ml of concentrated Milk Thistle seed extract with glycerin base.

Ten capsules are placed in a jar in 100 percent moisture and 40° C. condition for 90 days. The capsules maintained their stability.

Example 7

Preparation of Milk Thistle seed liquid capsule:

Standardized Milk Thistle seed powder extract (standardized to 80% of silymarins) obtained from concentration of aqueous alcoholic liquid extract, which is produced with percolation and/or maceration of the seed with alcohol and spring water.

An amount of 7.5 kg of Milk Thistle seed dry powder extract is placed in a 100 L reactor and/or extractor with heating jacket. To this is added 30 L of grain ethanol (with a concentration of at least 80 percent), 10 L glycerin and 10 L lecithin. Heat the reactor and/or extractor to 65–75° C. and refluxed for 2 hour at atmosphere pressure. The mixture of the Milk Thistle seed powder extract, grain alcohol and spring water is then concentrated with thin film evaporator until it has a moisture content of 5 percent or less.

The concentrated extract is removed from the flask and poured into a container. To this, 10 L of glycerin is added. The concentrated mixture is mixed and a sample is sent for testing. The concentration of silymarins in this extract should be at least 188 mg/ml. The volume is adjusted with a mixture of lecithin and glycerin (1:1) in accordance with the test results. The finished product has a volume of 31 L.

The extract is encapsulated in a size "0" vegetable capsule and sealed with the same gelatin. Each capsule holds 0.64 ml of the Milk Thistle seed extract.

Ten capsules are placed in a jar in 100 percent moisture and 40° C. condition for 90 days. The capsules maintained their stability.

Example 8

Preparation of Valerian liquid capsule:

Valerian aqueous alcoholic liquid extract is obtained from percolation and/or maceration of the herb with grain alcohol and spring water. The concentration of Valerenic acid in this liquid extract is 1.25 mg/ml.

A 100 L round bottom-flask is loaded with 10 L of glycerin. To this 355 L of Valerian root aqueous alcoholic liquid extract are injected and condensed until the extract has a moisture content of 5 percent or less.

The concentrated extract is removed from the flask and poured into a stainless-steel container. 20 L of glycerin is then added to the mixture and stirred well. A sample is sent for testing and the volume is adjusted in accordance with the test results. The concentration of Valerenic acid in the final product is 1.25 mg/ml. The ideal volume of the final product is 35 L.

The extract is encapsulated in a size "0" vegetable capsule and sealed with the same gelatin. Each capsule holds 0.64 ml.

Ten capsules are placed in a jar in 100 percent moisture and 40° C. condition for 90 days. The capsules maintained their stability.

Example 9

Preparation of Siberian Ginseng liquid capsule:

Standardized Siberian Ginseng powder extract obtained from concentration of aqueous alcoholic liquid extract, which is produced with percolation and/or maceration of the Siberian Ginseng root with alcohol and spring water.

An amount of 26 kg of Siberian Ginseng dry powder extract is placed in a 100 L reactor and/or extractor with heating jacket. To this is added 30 L of aqueous grain ethanol (with a concentration of 30–40 percent), 15 L glycerin. Heat the reactor and/or extractor to 65–75° C. and refluxed for 2 hour at atmosphere pressure. The mixture of the Siberian Ginseng powder extract, grain alcohol and spring water is then concentrated with thin film evaporator until it has a moisture content of 5 percent or less.

The concentrated extract is removed from the flask and poured into a stainless steel container. To this is added 30 L of glycerin. The concentrated mixture is mixed and a sample is sent for testing. The concentration of eleutheroside B and eleutheroside E in this extract should be at least 3.9 mg/ml. The volume is adjusted with glycerin in accordance with the test results. The finished product has a volume of 57 L.

The extract is encapsulated in a size "1" vegetable capsule and sealed with the same gelatin. Each capsule holds 0.41 ml of the Siberian Ginseng extract.

Ten capsules are placed in a jar in 100 percent moisture and 40° C. condition for 90 days. The capsules maintained their stability.

Example 10

Preparation of St. Johns Wort flower bud liquid capsule:

St. Johns Wort flower bud aqueous alcoholic liquid extract is obtained from percolation and/or maceration of the St. Johns Wort flower buds with grain alcohol and spring water. The concentration of Hypericins in this liquid extract is 0.3 mg/ml.

The aqueous alcoholic liquid St. Johns Wort flower bud extract is filtered through a screen (100 mesh).

A 100 L round bottom flask is loaded with 10 L of glycerin. To this 294 L (78 gallons) of St. John's Wort extract are injected gradually and condensed until the extract has a moisture content of 5 percent or less.

The concentrated extract is removed from the flask. 30 L of glycerin is added to the concentrated extract and mixed well.

A sample is sent for testing and the volume of the extract is adjusted in accordance with the test results to a finished volume of 57 L. The concentration of the hypericins in the extract will be 2.2 mg/ml.

The extract is encapsulated in a size "1" vegetable capsule and sealed with the same gelatin. Each capsule holds 0.41 ml of St. John's wort flower bud extract.

Ten capsules are placed in a jar in 100 percent moisture and 40° C. condition for 90 days. The capsules maintained their stability.

Example 11

Preparation of St. John's Wort supreme liquid capsule:

The aqueous alcoholic liquid extracts in the St. John's Wort supreme is obtained from percolation and/or maceration of the herbs with grain alcohol and spring water in a different concentration. The concentration of Hypericins in the St. John's Wort flower bud liquid extract is 0.3 mg/ml; the concentration of Kavalactones in Kava Kava liquid extract is 50 mg/ml; the Siberian Ginseng is 3.9 mg/ml for eleutheroside B and E; the Gotu Kola is 2 mg/ml for triterpenoids.

The following materials are used:

|  | L |
| --- | --- |
| St. John's wort extract | 108 |
| Kava kava solid extract | 56 |
| Milky seed oat extract | 15 |
| Passion flower extract | 28 |
| Gotu Kola extract | 15 |
| Schizandra extract | 15 |
| Siberian Ginseng solid extract | 15 |
| Nettle seed extract | 15 |
| Calamus extract | 9.5 |
| Prickly Ash Bark extract | 9.5 |

A 100 L flask is loaded with 15 L glycerin and to this flask, 286 L of all the above extracts are gradually injected and condensed until the extract has a moisture content of 5 percent or less.

The concentrated extract is removed from the flask. To the extract, 40 L glycerin is added.

A sample is sent for testing. The volume of the extract is adjusted in accordance with the test results to a finished volume of 64 L. The concentration of hypericins is 0.5 mg/ml and the concentration of kavalactones is 43 mg/ml.

The extract is encapsulated in a size "1" vegetable capsule and sealed with the same gelatin. Each capsule holds 0.41 ml of St. John's Wort Supreme.

Ten capsules are placed in a jar in 100 percent moisture and 40° C. condition for 90 days. The capsules maintained their stability.

Example 12

Preparation of Nettle leaf liquid capsule:

The Nettle leaf aqueous alcoholic liquid is obtained from percolation and/or maceration of the fresh Nettle leaf with grain alcohol and spring water. The concentration of caffeic acid and its derivatives in the Nettle leaf liquid extract is 0.32 mg/ml. The following materials is used:

|  | L |
| --- | --- |
| Nettle leaf aqueous alcoholic extract | 469 |

A 100 L flask is loaded with 10 L glycerin and to this flask, 900 L of all the above extracts are gradually injected and condensed until the extract has a moisture content of 5 percent or less.

The concentrated extract is removed from the flask. To the extract, 10 L glycerin is added.

A sample is sent for testing. The volume of the extract is adjusted in accordance with the test results to a finished volume of 29.5 L. The concentration of caffeic acid and its derivatives is 5 mg/ml.

The extract is encapsulated in a size "1" vegetable capsule and sealed with the same gelatin. Each capsule holds 0.41 ml of Nettle leaf extract.

Ten capsules are placed in a jar in 100 percent moisture and 40° C. condition for 90 days. The capsules maintained their stability.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A process for providing non-lipid, liquid form herbal extracts in cellulose derivative capsules, the process comprising the steps of:
    (a) extracting an herbal plant material with an aqueous alcohol to provide a aqueous alcoholic herbal extract;
    (b) adding sufficient glycerin to the aqueous alcohol herbal extract to maintain the herbal extract in solution or dispersed in the alcohol mixture;
    (c) removing alcohol and water from the aqueous alcoholic herbal extract to provide glycerin base liquid or semi-soft form herbal extract having a moisture content of less than 10 percent by weight; and
    (d) encapsulating the herb extract having a moisture content of less than 10 percent by weight in a cellulose derivative capsule.

2. The process of claim 1, whereby the herbal plant material is selected from the group consisting of kava kava, echinacea, St. John's wort, valerian root, milk thistle seed, Siberian ginseng, nettle leaf, ginkgo, gotu kola, ginkgo/gotu kola supreme, astragalus, goldenseal, dong quai, ginseng, St. John's wort supreme, echinacea/goldenseal supreme, bilberry, green tea, hawthorne, ginger, turmeric, black cohosh, cats claw, chamomile, dandelion, chaste tree berry, feverfew, garlic, horse chestnut, licorice, eyebright, yohimbe, astragalus supreme, valerian poppy supreme, and serenity elixir.

3. The process of claim 1, whereby bio-activity of the herbal extract is measured after step (a).

4. The process of claim 1, whereby bio-activity of the herbal extract is measured after step (c).

5. The process of claim 1, whereby the moisture content of the herbal extract is less than 5 percent by weight.

6. The process of claim 1, further including the step (e) of eliminating air in the cellulose derivative capsule by contacting the capsule with an inert gas.

7. A process for providing non-lipid, liquid form herbal extracts in vegetable gelatin or hydroxylalkylcellulose capsules, the process comprising the steps of:
    (a) extracting an herbal plant material with an aqueous alcohol to provide a aqueous alcoholic herbal extract;
    (b) adding sufficient glycerin to the aqueous alcohol herbal extract to maintain the herbal extract in solution or dispersed in the alcohol mixture;
    (c) removing alcohol and water from the aqueous alcoholic herbal extract to provide glycerin base liquid or semi-soft form herbal extract having a moisture content of less than 10 percent by weight; and
    (d) encapsulating the herb extract having a moisture content of less than 10 percent by weight in a vegetable gelatin, or hydroxyalkyl cellulose capsule.

8. The process of claim 7, whereby the hydroxylalkylcellulose is hydroxypropyl methylcellulose.

9. The process of claim 7, whereby the herbal plant material is selected from the group consisting of kava kava, echinacea, St. John's wort, valerian root, milk thistle seed, Siberian ginseng, nettle leaf, ginkgo, gotu kola, ginkgo/gotu kola supreme, astragalus, goldenseal, dong quai, ginseng, St. John's wort supreme, echinacea/goldenseal supreme, bilberry, green tea, hawthorne, ginger, turmeric, black cohosh, cats claw, chamomile, dandelion, chaste tree berry, feverfew, garlic, horse chestnut, licorice, eyebright, yohimbe, astragalus supreme, valerian poppy supreme, and serenity elixir.

10. The process of claim 7, whereby bio-activity of the herbal extract is measured after step (a).

11. The process of claim 7, whereby bio-activity of the herbal extract is measured after step (c).

12. The process of claim 7, whereby the moisture content of the herbal extract is less than 5 percent by weight.

13. The process of claim 7, further including the step (e) of eliminating air in the cellulose derivative capsule by contacting the capsule with an inert gas.

14. The process of claim 13, whereby the inert gas is nitrogen.

* * * * *